United States Patent [19]
Kudo et al.

[11] 3,935,282
[45] Jan. 27, 1976

[54] PROCESS FOR PREPARATION OF α-NAPHTHOL

[75] Inventors: Ken-ichi Kudo, Niihama; Tadayuki Ohmae, Kobe; Akihiko Uno, Toyonaka, all of Japan

[73] Assignee: Sumitomo Chemical Company, Ltd., Osaka, Japan

[22] Filed: May 6, 1974

[21] Appl. No.: 467,541

[52] U.S. Cl. ............................................ 260/621 H
[51] Int. Cl.² ............................................ C07C 39/14
[58] Field of Search ............ 260/621, 621 H, 621 R; 252/471

[56] References Cited
UNITED STATES PATENTS

| | | | |
|---|---|---|---|
| 2,848,510 | 8/1958 | Myers et al. | 252/471 |
| 3,354,231 | 11/1967 | Maloy et al. | 260/621 H |
| 3,378,591 | 4/1968 | Freure | 260/621 H |

*Primary Examiner*—James O. Thomas, Jr.
*Assistant Examiner*—W. B. Lone
*Attorney, Agent, or Firm*—Sughrue, Rothwell, Mion, Zinn & Macpeak

[57] ABSTRACT

α-Naphthol is prepared by dehydrogenating α-Tetralone in the presence of a catalyst comprising (1) platinum or a platinum compound, (2) an alkali metal salt, and (3) a manganese compound and/or a chromium compound supported on a gamma-type alumina carrier. By using such catalyst, the conversion of α-Tetralone is markedly increased, and the catalyst life is very much prolonged.

3 Claims, 2 Drawing Figures

PROCESS FOR PREPARATION OF α-NAPHTHOL

BACKGROUND OF THE INVENTION

1. Field of the Invention

This invention relates to a process for preparing α-naphthol by dehydrogenating ketotetrahydronaphthalene (to be referred to herein for brevity as "α-Tetralone," a well-known registered trademark), and more specifically, to a process for preparing α-naphthol which comprises dehydrogenating α-Tetralone using a catalyst comprising (1) platinum or a platinum compound, (2) an alkali metal salt and (3) a manganese compound and/or a chromium compound supported on a gamma-type alumina carrier.

2. Description of the Prior Art

α-Naphthol is a very important industrial material useful, for example, as dye intermediates or raw materials for agricultural chemicals.

A number of studies have previously been made on methods for preparing α-naphthol. Typical prior art techniques are methods such as the alkali fusion of α-chloronaphthalene and the hydrolysis of α-naphthalenesulfonic acid. These methods, however, are not free from the formation of β-naphthol as a by-product, and therefore, the resulting product is contaminated with a certain amount of such by-products. Furthermore, these known methods are disadvantageous for commercial mass-production because an undesirable procedure such as alkali fusion is employed. The production of α-naphthol by the dehydrogenation reaction of α-Tetralone is described, for example, in U.S. Pat. No. 3,378,591, but the catalyst used in the method disclosed therein has a short lifetime and is disadvantageous as a commercial method.

Lengthy studies on methods for producing α-naphthol by the dehydrogenation reaction of α-Tetralone as a starting material in the presence of a catalyst comprising various kinds of metals or compounds thereof supported on alumina have been made to arrive at the present invention.

SUMMARY OF THE INVENTION

According to this invention, therefore, there is provided a process for preparing α-naphthol, which comprises dehydrogenating α-Tetralone in the presence of a catalyst comprising (1) platinum or a platinum compound, (2) an alkali metal salt, and (3) a manganese compound and/or a chromium compound supported on a γ-alumina carrier.

BRIEF DESCRIPTION OF THE ACCOMPANYING DRAWINGS

FIGS. 1 and 2 show the typical pore size distribution of an ordinary aluminum carrier and a preferred aluminum carrier, respectively.

DETAILED DESCRIPTION OF THE INVENTION

According to the process of this invention, the conversion of α-Tetralone is remarkably improved and the activity of the catalyst is extremely lengthened, as compared with the method disclosed in the above-cited U.S. Pat. Thus, the process of this invention is a very advantageous commercial process for producing α-naphthol.

The platinum compound used as one active component of the catalyst can, for example, be chloroplatinic acid, or its salts such as sodium chloroplatinate.

Examples of alkali metal salts which can be used as the second active component of the catalyst are sodium sulfate, sodium carbonate, sodium acetate, sodium chloride, and sodium chloroplatinate.

Examples of manganese compounds which can be used as the third active component of the catalyst are manganous sulfate, manganous chloride, manganous nitrate, manganous acetate, manganic sulfate, and sodium permanganate. Examples of chromium compounds which can be used as the third active component of the catalyst include chromous sulfate, chromous acetate, chromic chloride, chromium trioxide, and sodium bichromate.

It is apparent that the carrier should be one capable of maintaining the activity of the catalyst at a high level. In the preparation of the catalyst composition used in this invention, γ-alumina is used as a carrier.

Based on the information that the pore diameter of a carrier exerts influences on the catalytic activity, conversion, selectivity and catalyst life in a catalytic reaction, extensive studies have been made on the dehydrogenation reaction in accordance with this invention of α-Tetralone in the presence of the specific catalyst composition described above to prepare α-naphthol. Although, it is well known that micropores (pores having a pore diameter of not more than 100 A) are important factors for the activity and selectability of the catalyst composition it has been found that macropores (pores having a pore diameter of more than 100 A) significantly influence the conversion of α-Tetralone, the selectivity to α-naphthol, and the catalyst life. Specifically, we have found that by selecting alumina using as a carrier on the basis of the distribution of macropores and the ratio of the macropore volume to the total pore volume of the carrier, the yield of α-naphthol is increased, and the catalyst life is remarkably lengthened.

Thus, it is more preferable to use γ-alumina as a carrier material containing micropores and, at the same time, having a pore diameter distribution from 100 A to 75,000 A, that is, having a macropore volume of at least 0.2 cm$^3$/g, preferably at least 0.3 cm$^3$/g.

Figure 2:
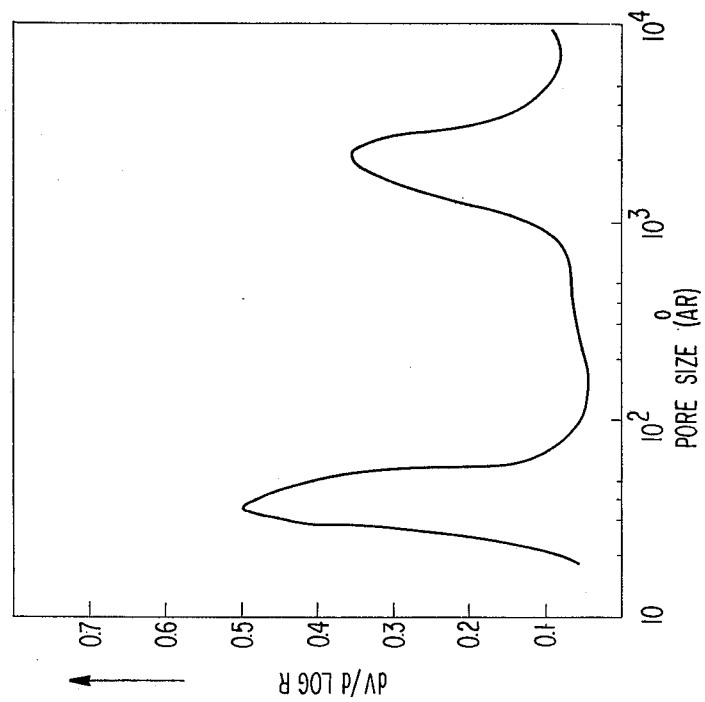
Figure 1:
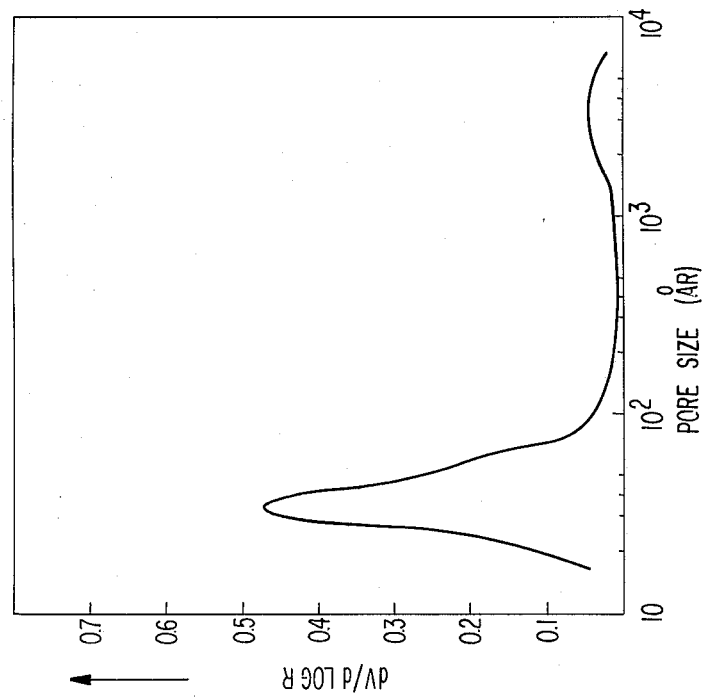

The pore size distribution of the alumina carrier is measured by means of a porosimeter (Aminco 60,000 psi). The typical pore diameter distribution of an ordinary alumina carrier as used in this invention is shown in FIG. 1 of the accompanying drawings, and that of a preferred alumina carrier as used in this invention which has macropores is shown in FIG. 2.

There is no particular restriction on the method of supporting the active catalyst components on the alumina carrier, and any of those methods generally employed can be used. For example, the γ-alumina carrier, preferably one having a macropore distribution as defined above, can be immersed in an aqueous solution having the catalyst components employed in this invention dissolved therein, and the volatile substances are removed at atmospheric or reduced pressure at room temperature or at an elevated temperature, thereby to support these catalyst components on the γ-alumina carrier. Alternatively, the first, second and third catalyst components can be supported sequentially on the γ-alumina carrier. In addition, the γ-alumina carrier can be immersed in an aqueous solution of the first component for a certain period of time, and the first component is then reduced using a conventional reducing agent such as hydrazine, formaldehyde or hydrogen, after which the second and third components are supported.

The amount of the catalyst supported is not particularly limited, and usually, it is 0.1 to 5.0% by weight, preferably 0.1 to 1.0% by weight as platinum, 0.1 to 4.0% by weight, preferably 0.1 to 2.0% by weight, as the alkali metal, and 0.1 to 5.0% by weight as manganese and/or chromium.

The $\alpha$-Tetralone used as a starting material is usually of pure quality. At times, however, starting materials containing more than 20% $\alpha$-Tetralone, or starting materials containing naphthalene can also be used, and there is no particular limitation on the content of the impurities except that catalyst poisoning impurities should not be present.

In practice, the supported catalyst prepared by the method described above is charged into a reaction zone such as a tubular reactor having a suitable length and a suitable diameter and activated by heating at 200° to 400°C for 10 to 30 hours under a stream of hydrogen. Then, the starting material $\alpha$-Tetralone is continuously fed together with hydrogen into the reaction tube and the dehydrogenation reaction is carried out by contacting the reactant with the catalyst at an elevated temperature under atmospheric or pressurized conditions.

The reaction temperature is 200° to 450°C, preferably 330° to 410°C. The reaction pressure is normal atmospheric pressure or higher. Usually, it is advantageous to operate at about normal atmospheric pressures.

The amount of the starting $\alpha$-Tetralone to be fed is not particularly limited, but usually, it is 0.3 to 5.0 liters/liter of catalyst/hour, preferably 0.4 to 2.0 liters/liter of catalyst/hour.

Hydrogen is preferably used as a carrier gas. The molar ratio of $H_2/\alpha$-Tetralone ranges from 0.5 to 15, preferably 2.0 to 6.0.

According to the process of this invention, since the catalyst life is extremely prolonged as compared with the known conventional catalysts, the number of regenerations and rechargings of the catalyst can be minimized, and the process of this invention is very advantageous commercially.

The following Examples are illustrative of preferred embodiments of the present invention with Comparative Examples shown at the same time. It will be understood that these examples are given for the purposes of illustration and the present invention is not to be interpreted as limited to those examples. Unless otherwise indicated, all parts, ratios and percents are by weight.

EXAMPLE 1

Anhydrous sodium sulfate (0.14 g), 0.44 g of anhydrous sodium carbonate and 0.35 g of chromium trioxide were dissolved in 31 g of water, and 1.5 ml of an aqueous solution of chloroplatinic acid (platinum content 12.1 g/100 ml) was further added. 18 g of spherical $\gamma$-alumina (average diameter 3 mm, bulk density 0.55 g/cm$^3$, specific surface area 150 m$^2$/g) was immersed in the resulting aqueous solution for 24 hours. Then, water was removed while rotating the mixture under heat at reduced pressure, thereby to form a dry carrier-supported catalyst containing 1.0% by weight of platinum, 1.32% by weight of sodium ion, 0.54% by weight of sulfate, and 1.0% by weight of chromium.

30 ml of the catalyst thus obtained was packed in a stainless steel reaction tube with an inside diameter of 18 mm and a length of 400 mm, and activated in a stream of hydrogen at 370°C for 15 hours. Then, $\alpha$-Tetralone and hydrogen were continuously fed into the reaction tube at a flow rate of 20 ml/hour and 180 ml/hour, respectively, and they were contacted with the catalyst at a reaction temperature of 360°C under atmospheric pressure. With the lapse of time, the conversion of $\alpha$-Tetralone and the selectivity to $\alpha$-naphthol changed as shown in Table 1 below.

Table 1

| Lapse of Time | Conversion of $\alpha$-Tetralone | Selectivity for $\alpha$-naphthol |
|---|---|---|
| (hours) | (mol %) | (mol %) |
| 10 | 90 | 94 |
| 100 | 89 | 95 |
| 200 | 87 | 98 |
| 300 | 86 | 98 |
| 400 | 85 | 98 |
| 500 | 85 | 98 |

COMPARATIVE EXAMPLE 1

A catalyst containing 1.0% by weight of platinum, 1.32% by weight of sodium ion and 0.54% by weight of sulfate supported on $\gamma$-alumina was prepared in the same way as described in Example 1 except that chromium trioxide was not used.

$\alpha$-Tetralone was dehydrogenated in the same way as in Example 1 using a catalyst obtained as described in Example 1 above except that the activation of the catalyst was performed for 150 hours, and the flow rate of hydrogen was changed to 150 ml/min. The results obtained are shown in Table 2.

Table 2

| Lapse of Time | Conversion of $\alpha$-Tetralone | Selectivity for $\alpha$-naphthol |
|---|---|---|
| (hours) | (mol %) | (mol %) |
| 10 | 88 | 96 |
| 100 | 86 | 97 |
| 200 | 81 | 98 |
| 300 | 77 | 98 |
| 400 | 73 | 98 |
| 500 | 67 | 98 |

EXAMPLE 2

Manganese acetate tetrahydrate (0.80 g) and 1.40 g of sodium acetate trihydrate were dissolved in 31 g of water, and 1.5 ml of an aqueous solution of chloroplatinic acid (platinum content 12.1 g/100 ml) was further added. 18 g of the same spherical $\gamma$-alumina as used in Example 1 was immersed in the resulting aqueous solution for 24 hours. Then, by the same procedure as used in Example 1, a catalyst containing 1.0% by weight of platinum, 1.32% by weight of sodium ion and 1.0% by weight of manganese supported on the $\gamma$-alumina was obtained.

Using 30 ml of the catalyst obtained above, dehydrogenation of $\alpha$-Tetralone was performed under the same reaction conditions as in Comparative Example 1. The results obtained are shown in Table 3 below.

Table 3

| Lapse of Time | Conversion of $\alpha$-Tetralone | Selectivity for $\alpha$-naphthol |
|---|---|---|
| (hours) | (mol %) | (mol %) |
| 10 | 91 | 83 |
| 100 | 90 | 88 |
| 200 | 89 | 92 |

Table 3-continued

| Lapse of Time | Conversion of α-Tetralone | Selectivity for α-naphthol |
| --- | --- | --- |
| (hours) | (mol %) | (mol %) |
| 300 | 87 | 93 |
| 400 | 86 | 93 |
| 500 | 85 | 96 |

EXAMPLE 3

Manganese acetate tetrahydrate (0.40 g) and 1.40 g of sodium acetate trihydrate were dissolved in 31 g of water, and 1.5 ml of an aqueous solution of chloroplatinic acid (platinum content 12.1 g/100 ml) was further added. 18 g of the same spherical γ-alumina as used in Example 1 was immersed in the resulting aqueous solution for 24 hours, and then using the same procedure as used in Example 1, a catalyst containing 1.32% by weight of sodium ion, 1.0% by weight of platinum and 0.5% by weight of manganese supported on γ-alumina was obtained. Using 30 ml of this catalyst, dehydrogenation of α-Tetralone was performed under the same conditions as used in Example 1. The results obtained are shown in Table 4.

Table 4

| Lapse of Time | Conversion of α-Tetralone | Selectivity for α-naphthol |
| --- | --- | --- |
| (hours) | (mol %) | (mol %) |
| 10 | 91 | 84 |
| 100 | 90 | 92 |
| 200 | 88 | 94 |
| 300 | 87 | 95 |
| 400 | 85 | 95 |
| 500 | 85 | 96 |

EXAMPLE 4

Chromium trioxide (0.17 g), 0.40 g of manganese acetate tetrahydrate and 1.40 g of sodium acetate trihydrate were dissolved in 31 g of water, and 1.5 ml of an aqueous solution of chloroplatinic acid (platinum content 12.1 g/100 ml) was further added. 18 g of the same γ-alumina as used in Example 1 was immersed in the resulting aqueous solution for 24 hours, and then using the same procedure as described in Example 1, a catalyst containing 1.0% by weight of platinum, 1.32% by weight of sodium ion, 0.5% by weight of chromium and 0.5% by weight of manganese supported on γ-alumina was obtained. Using 30 ml of this catalyst, dehydrogenation of α-Tetralone was performed under the same conditions as described in Example 1. The results obtained are shown in Table 5.

Table 5

| Lapse of Time | Conversion of α-Tetralone | Selectivity for α-naphthol |
| --- | --- | --- |
| (hours) | (mol %) | (mol %) |
| 10 | 91 | 88 |
| 100 | 90 | 92 |
| 200 | 88 | 95 |
| 300 | 86 | 96 |
| 400 | 85 | 96 |
| 500 | 84 | 97 |

While the invention has been described in detail and with reference to specific embodiments thereof, it will be apparent to one skilled in the art that various changes and modifications can be made therein without departing from the spirit and scope thereof.

What is claimed is:

1. A process for preparing α-naphthol, which consists essentially of dehydrogenating ketotetrahydronaphthalene at a temperature of from 200 to 450°C at from atmospheric pressure to a slightly elevated pressure, in the presence of a catalyst comprising (1) platinum or a platinum compound selected from the group consisting of chloroplatinic acid and the salts thereof; (2) an alkali metal salt selected from the group consisting of sodium sulfate, sodium carbonate, sodium acetate, sodium chloride and sodium chloroplatinate; and (3) a maganese compound selected from the group consisting of maganous sulfate, manganous chloride, manganous nitrate, manganous acetate, manganic sulfate and sodium permanganate and/or a chromium compound selected from the group consisting of chromous sulfate, chromous acetate, chromic chloride, chromium trioxide and sodium bichromate; supported on a γ-alumina carrier.

2. The process of claim 1, wherein said γ-alumina carrier has a macropore volume of at least 0.2 cm³/g.

3. The process of claim 1, wherein said catalyst contains 0.1 to 5.0% by weight as platinum of said platinum or said platinum compound, 0.1 to 4.0% by weight as alkali metal of said alkali metal salt and 0.1 to 5.0% by weight as manganese and/or as chromium of said manganese compound and/or said chromium compound supported on said γ-alumina carrier.

* * * * *